United States Patent [19]

Menon et al.

[11] Patent Number: 5,391,497
[45] Date of Patent: Feb. 21, 1995

[54] HUMAN K-CASEIN

[75] Inventors: Ravi S. Menon, Lafayette; Kathleen F. Jeffers, Denver; Ying-Fon Chang, Arvanda; Richard G. Ham, Boulder, all of Colo.

[73] Assignee: University of Colorado Foundation, Inc., Boulder, Colo.

[21] Appl. No.: 962,569

[22] Filed: Oct. 13, 1992

[51] Int. Cl.6 .................. A23J 1/20; A61K 37/16; C07K 3/00; C07K 13/00
[52] U.S. Cl. .................. 435/320.1; 435/69.1; 530/361; 530/360; 536/22.1; 536/23.5
[58] Field of Search .................. 435/69.1, 320.1; 530/360; 536/22.1, 23.5

[56] References Cited

PUBLICATIONS

Bugnon et al. "Preparation and amino acid . . . " Feb. Lett. 188-1 pp. 48-54 1985.

Glaver "Principles of Cloning DNA" Gene Cloning, p. 1-20 1984.

Earl et al. "Monoclonal antibodies . . . " Mol. Imm. vol. 22, No. 8 pp. 981-991 1985.

*Primary Examiner*—Keith Baker
*Assistant Examiner*—Hyosuk Kim
*Attorney, Agent, or Firm*—Frederick W. Pepper

[57] ABSTRACT

A cDNA sequence encoding human κ-casein.

4 Claims, 5 Drawing Sheets

SCHEMATIC REPRESENTATION OF CLONES IN RELATION TO FULL-LENGTH cDNA SEQUENCE

Fig. 5

```
GCCTGGTGAT AGCTGGTTGT CCAAGATAGA ATCTTAGTTC AACTTTAAAT TTGCCAGCTC      60

AACCTACTGC CAACCAAGAC CTGACTGGCA CGAGGAAGGT GCAATA ATG AAG AGT        115
                                                  Met Lys Ser
                                                   1

TTT CTT CTA GTT GTC AAT GCC CTG GCA TTA ACC CTG CCT TTT TTG GCT       163
Phe Leu Leu Val Val Asn Ala Leu Ala Leu Thr Leu Pro Phe Leu Ala
     5                   10                  15

GTG GAG GTT CAA AAC CAG AAA CAA CCA GCA TGC CAT GAG AAT GAT GAA       211
Val Glu Val Gln Asn Gln Lys Gln Pro Ala Cys His Glu Asn Asp Glu
 20              25                  30                  35

AGA CCA TTC TAT CAG AAA ACA GCT CCA TAT GTC CCA ATG TAT TAT GTG       259
Arg Pro Phe Tyr Gln Lys Thr Ala Pro Tyr Val Pro Met Tyr Tyr Val
             40                  45                  50

CCA AAT AGC TAT CCT TAT TAT GGA ACC AAT TTG TAC CAA CGT AGA CCA       307
Pro Asn Ser Tyr Pro Tyr Tyr Gly Thr Asn Leu Tyr Gln Arg Arg Pro
             55                  60                  65

GCT ATA GCA ATT AAT AAT CCA TAT GTG CCT CGC ACA TAT TAT GCA AAC       355
Ala Ile Ala Ile Asn Asn Pro Tyr Val Pro Arg Thr Tyr Tyr Ala Asn
             70                  75                  80

CCA GCT GTA GTT AGG CCA CAT GCC CAA ATT CCT CAG CGG CAA TAC CTG       403
Pro Ala Val Val Arg Pro His Ala Gln Ile Pro Gln Arg Gln Tyr Leu
 85                  90                  95

CCA AAT AGC CAC CCA CCC ACT GTG GTA CGT CGC CCA AAC CTG CAT CCA       451
Pro Asn Ser His Pro Pro Thr Val Val Arg Arg Pro Asn Leu His Pro
100                 105                 110                 115

TCA TTT ATT GCC ATC CCC CCA AAG AAA ATT CAG GAT AAA ATA ATC ATC       499
Ser Phe Ile Ala Ile Pro Pro Lys Lys Ile Gln Asp Lys Ile Ile Ile
                120                 125                 130

CCT ACC ATC AAT ACC ATT GCT ACT GTT GAA CCT ACA CCA ACT CCT GCC       547
Pro Thr Ile Asn Thr Ile Ala Thr Val Glu Pro Thr Pro Thr Pro Ala
            135                 140                 145

ACT GAA CCA ACG GTG GAC AGT GTA GTC ACT CCA GAA GCT TTT TCA GAG       595
Thr Glu Pro Thr Val Asp Ser Val Val Thr Pro Glu Ala Phe Ser Glu
            150                 155                 160

TCC ATC ATC ACG AGC ACC CCT GAG ACA ACC ACA GTC GCA GTT ACT CCA       643
Ser Ile Ile Thr Ser Thr Pro Glu Thr Thr Thr Val Ala Val Thr Pro
165                 170                 175

CCT ACG GCA TAA A AACACCAAGG AAATATCAAA GAACACAACG CAGGACTTGC         696
Pro Thr Ala *
180

TGAAACCAAA TTACTACTTC ACACTCTCCT GCAGCCATTG TCTGCCTTCA GTCAACAGAA     756

ATGTGATTTT CACAGATTCA GCTCTTCTCT CCTTACATTT TACATTCATG CCACATTCAA     816

TATTTTGATT CTTGCACAAT AAAGCCAACT GATTGCAACC TG                        858
```

HUMAN K-CASEIN

The U.S. Government has a paid-up license in this invention and the right in limited circumstances to require the patent owner to license others on reasonable terms as provided for by the terms of contract No. CA 30028 awarded by the National Cancer Institute.

FIELD OF THE INVENTION

The present invention relates to the human milk protein κ-casein produced by recombinant DNA techniques.

BACKGROUND OF THE INVENTION

The predominant milk proteins in mammals are the caseins, secretory phosphoproteins synthesized during lactation. The caseins are the main source of amino acids for the nursing infant. In addition, the caseins transport the amount of calcium phosphate needed in milk for infant bone formation. The caseins, by forming micelles which entrap calcium phosphate, raise the calcium and phosphate concentrations in milk to levels well in excess of the solubility product of calcium phosphate. Among the caseins, κ-casein is required for stabilizing the casein micellar structures against precipitation. Besides stabilizing micelles, κ-casein has a labile peptide bond in its primary structure susceptible to cleavage by low amounts of the protease rennin which results in milk clotting. Such milk clotting increases the retention time of milk in the intestines which is believed to be of nutritional value in young animals.

Many human infants unable to be breast-fed by their mothers experience severe digestive disturbances when fed milk from dairy animals or various alternative non-milk formulas. In fact, the onset of juvenile diabetes in infants genetically predisposed to the disease may be caused by their immune response to proteins found in cow's milk (Karajalainen et al., Mew Eng. J. Med. 327: 302–307 (1992)). Only through recombinant DNA techniques can large quantities of human milk protein be made available for those infants susceptible to severe digestive disturbances and possibly juvenile diabetes.

Therefore, a need arises to isolate DNA sequences of human milk proteins for obtaining such proteins in large quantities. It is especially desirable to have available for infants large quantities of the human milk protein, κ-casein. At the present time only minute amounts of human κ-casein have been isolated by chromatographic means (Brignon et al., FEBS LETTERS 188: 48–54 (1985)).

One way to isolate a DNA sequence encoding a desired human milk protein such as κ-casein is via cDNA cloning. In this process, messenger RNA (mRNA) is isolated from cells known or suspected of producing the desired protein. Through a series of enzymatic reactions, the mRNA population of the cells is copied into a complementary DNA (cDNA). The resulting cDNA is then inserted into cloning vehicles and subsequently used to transform a suitable prokaryotic or eukaryotic host. The resultant gene library is comprised of a population of transformed host cells, each of which contain a single gene or gene fragment. The entire library, therefore, provides a representative sample of the coding information present in the mRNA mixture used as a starting material.

Gene libraries are screened using specific nucleic acid or antibody probes. Nucleic acid probes are useful for locating cDNAs by hybridization and autoradiography techniques. This approach, however, requires previous knowledge of at least a portion of the protein's amino acid or DNA-encoding sequence. Alternatively, methods have been developed to identify specific clones by probing recombinant gene libraries with antibodies specific for the encoded protein of interest. This method can be used with "expression vector" cloning vehicles since elaboration of the product protein is required. An example of this is the bacteriophage λ-gt11 system described by Young and Davis, Proc. Natl. Acad. Sci. 80:1194–1198 (1983).

Once the cDNA is isolated, the entire cDNA sequence information can be used to identify a full length gene for insertion into transgenic animals. This leads to the production of mature proteins.

SUMMARY OF THE INVENTION

In general, the invention features, in one aspect, a cDNA sequence encoding human κ-casein.

In another aspect, the invention features a vector, preferably a plasmid, containing a DNA sequence encoding human κ-casein.

The invention can permit the production of highly purified human κ-casein, without contamination from other human or animal milk proteins.

The cDNA of the invention is superior to genomic human κ-casein because the cDNA does not include untranslated introns, and therefore can be more easily used in prokaryotic host cells.

BRIEF DESCRIPTION OF THE DRAWINGS

FIG. 5 shows the complete nucleotide sequence SEQ ID NO:7 of the human κ-casein cDNA sequence with noncoding regions.

DETAILED DESCRIPTION OF THE INVENTION

Figure 1:
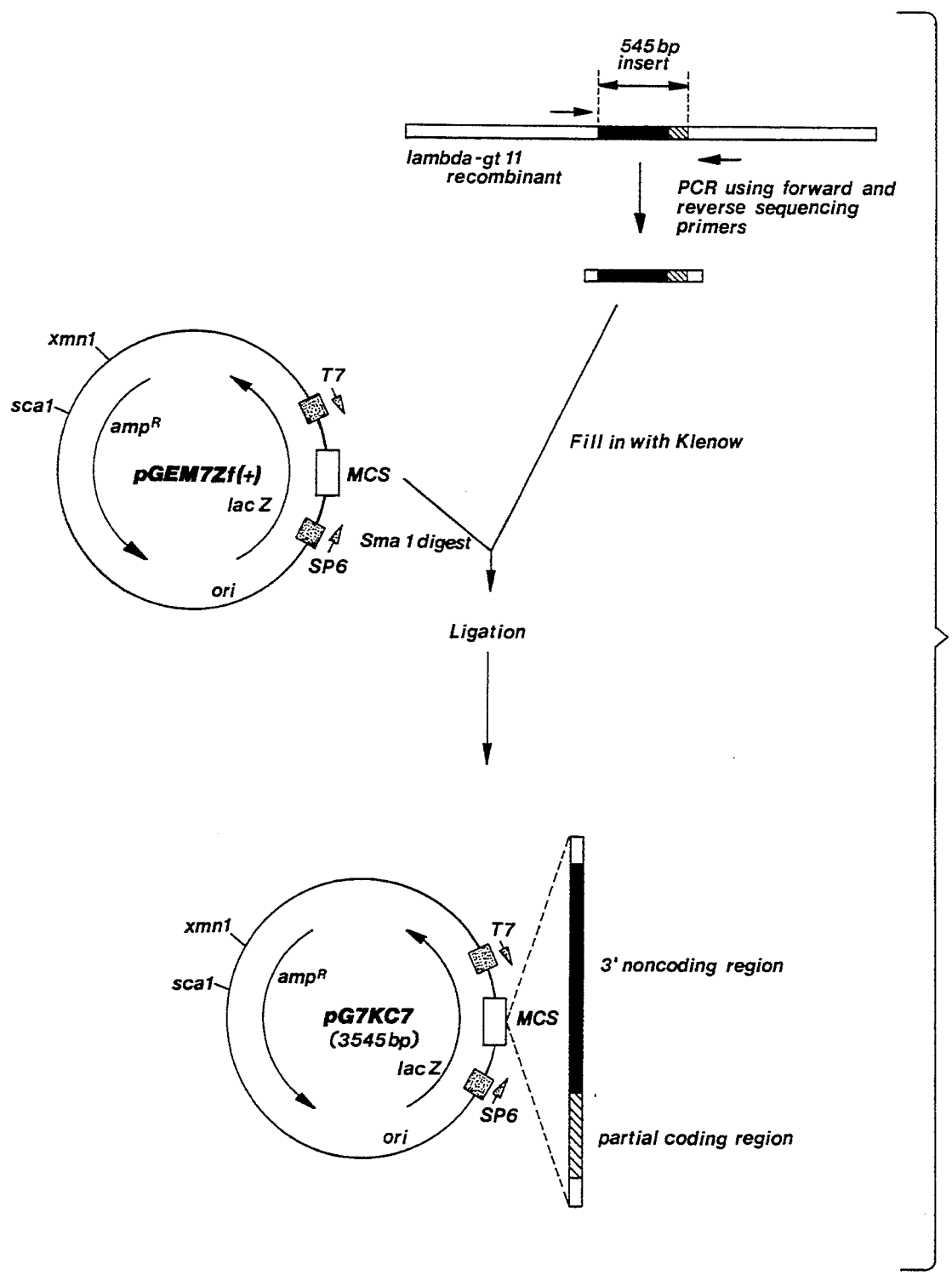
FIG. 1 shows the construction of a plasmid with a 545 bp cDNA insert coding for 113 C-terminal amino acids of the mature human κ-casein protein and containing the entire 3'-noncoding region.

"Expression vectors" refer to vectors which are capable of replicating and transcribing DNA sequences contained therein, where such sequences are linked to other regulatory sequences capable of affecting their expression. These expression vectors must be propagated in the host organisms or systems either as autonomous episomes or as an integral part of the chromosomal DNA.

One form of expression vector which is suitable for use in the invention is the bacteriophage, a virus which replicates in bacteria. The λ-gt11 phage is particularly desirable for this purpose. Lambda-gt11 is a general recombinant DNA expression vector capable of producing polypeptides specified by the inserted DNA. To minimize degradation, upon induction with a synthetic analog of lactose (IPTG), foreign proteins or portions thereof are synthesized as fused proteins with the prokaryotic protein D galactosidase. The use of host cells defective in protein degradation pathways may also increase the longevity of novel proteins produced from the induced λ-gt11 clones. Proper expression of foreign DNA in λ-gt11 clones will depend upon the proper orientation and reading frame of the inserted DNA with respect to the β-galactosidase gene. Another form of expression vector used in recombinant DNA techniques is the prokaryotic plasmid: an unintegrated (extrachromosomal), double-stranded DNA circle. A third class of expression vectors are the eukaryotic vectors: vectors capable of driving expression of the foreign DNA in a eukaryotic cell. These are generally derived from viral sources and may be either extrachromosomal or integrated. The invention includes any other form of expression vector which serves an equivalent function and which is or subsequently becomes known in the art.

Recombinant vectors and methodology disclosed herein are suitable for use in a wide range of prokaryotic and eukaryotic host cells. These host cells include microbial strains, such as *E. coli* INV1alphaF', *Saccharomyces cerevisiae*, and cell lines derived from multicellular eukaryotic organisms.

Human κ-casein cDNA clones are isolated from a commercial λ-gt11 expression library. This library is prepared with mRNA obtained from human breast tissue removed during the third trimester of pregnancy because of malignancy. Approximately 500,000 bacteriophage clones are screened with a rabbit polyclonal antibody to human κ-casein as described by Young and Davis, Proc. Natl. Acad. Sol. 80:1194–1198 (1983). Two positive plaques are isolated, expanded, and purified by techniques described by Sambrook et al., Molecular Cloning: A Laboratory Manual, Cold Spring Harbor Press, NY (1989). Phage DNA is isolated from large scale lysates of each of the positive phage cultures. The cDNA inserts from the positive phages are amplified by polymerase chain reaction (PCR) using oligonucleotide primers to regions flanking the site into which the cDNA insert is cloned. The larger of the two cDNA inserts (545 bp) is subcloned in the SmaI site of pGEM7Zf(+) (Promega Corp.), and sequenced as described below. The 545 bp cDNA insert is a partial clone, coding for 113 C-terminal amino acids of the mature protein, and the entire 3'-noncoding region. The eDNA library is rescreened with $^{32}$p-labeled RNA transcripts made from the partial cDNA clone as described by Yoshimura and Oka, Gene 78:267–275 (1989), in order to obtain full-length cDNA clones. Several putative positive clones are obtained, and plaques corresponding to these regions are analyzed for size of the cDNA inserts by PCR. The oligonucleotide primers used for estimating the insert sizes are the forward or reverse sequencing primer and an antisense primer to the region of κ-casein coding for amino acids 75 to 80. The anticipated length (350 bp) of the resulting product is deduced from the average length of the corresponding segment in other species. The plaque area, designated 1.2(1), yields a PCR product of approximately 350 bp with the forward sequencing primer. The PCR product is subcloned into the SmaI site of pGEM7Zf(+), and sequenced as described below. The recombinant plasmid, designated pG7kcl.2(1), contains the remaining nucleotide sequence for the full-length cDNA for human κ-casein.

The recombinant plasmids (circular double stranded templates) are sequenced with SEQUENASE (modified bacteriophage T7 DNA polymerase) in both directions by a modified Sanger dideoxy method using primers to regions immediately flanking the multiple cloning site (Kraft et al., BioTechniques 6:544–549 (1988)). For long inserts, that can not be sequenced in their entirety from the ends, synthetic oligonucleotide primers, used as sequencing primers, are synthesized based on the sequence information obtained from the previous run. This circumvents the need to subclone short overlapping restriction fragments to obtain the entire sequence of the insert.

The following example is presented to illustrate the present invention and to assist one of ordinary skill in making and using the same. The example is not intended in any way to otherwise limit the scope of the invention.

EXAMPLE

A. Isolation of eDNA Clones for Human κ-Casein

A commercial cDNA library (Clontech, Palo Alto, Calif.) prepared from mRNA obtained from human breast tissue removed during the third trimester of pregnancy was used to obtain cDNA clones for human κ-casein. The library contained approximately $1.6 \times 10^6$ independent cDNAs cloned into the EcoRI site of the λ-gt11 phage. Approximately $5 \times 10^5$ recombinant phages were plated at a density of 100,000 pfu/150 mm plate, on lawn of *E. coli* Y1090 (ATCC #37197) [*E. coli* ΔlacU169, proA+, lon araD139, strA, supF(trpC22::Tn10)(pMC9)] and incubated at 42° C. for 2 hr. The absence of the lon protease in this strain of *E. coli* reduces the degradation of foreign protein, and consequently maximizes the signal obtained from a positive clone. Nitrocellulose filters impregnated with 10mM isopropyl thio-B-d-galactopyranoside (IPTG), and blotted to remove excess IPTG solution, were overlaid on the plates, and the plates were incubated at 37° C. for 2 to 3 hours. The plates were then stored overnight at 4° C. The position of the filters on the plates were marked with a needle, and the filters were removed, dried for 30 minutes with the side of the filters in contact with the plates facing up. The plates were sealed and stored refrigerated. The filters were rinsed once with TBS (20 mM Tris-HCl pH 7.5 and 500 mM NaCl), and transferred to 3% (w/v) gelatin in TBS for 1 hr at room temperature. The filters were then transferred to Tween-TBS (TBS containing 0.05% Tween-20) containing rabbit anti-bovine κ-casein antibody (primary antibody) (provided by Dr. Harrold M. Farrell, USDA/ARS/Eastern Regional Research Center, Philadelphia, Pa.) at a 1:1000 dilution, and incubated at room temperature for 1 hour. The filters were then rinsed with Tween-TBS three times for 5 minute durations per wash and transferred to Tween-TBS containing anti-rabbit IgG tagged with alkaline phosphatase (secondary antibody; Bio-Rad Corp., Richmond, Calif.) at a 1:5000 dilution, and incubated at room temperature for 1 hour. The filters were rinsed with Tween-TBS for 5 minutes, followed by two 5-minute rinses with TBS alone. The filters were then transferred to 200 ml Tris-Mg buffer (100 mM Tris-HCl pH 9.5 and 0.5mM $MgCl_2$) containing 0.3 mg/ml nitro blue tetrazolium (NBT) and 0.15 mg/ml 5-bromo-4-chloro-3-indolyl phosphate (BCIP) and incubated at room temperature with gentle agitation for about 30 minutes. Clones that were positive appeared as small purple circles on the filter. In the first round of screening, two positive clones were obtained. The filters were then washed thoroughly with water, air dried, and stored between cellophane sheets to minimize bleaching of the signals.

Filters with positive signals were accurately positioned over the appropriate plate with the help of the needle marks made earlier, and the exact location of each positive phage clone on the plate was determined. A small area of the agar, including the positive clone was then removed and transferred to Phage Extraction Buffer (50 mM Tris-HCl pH 7.5, 100 mM NaCl, 8 mM MgCl$_2$, 0.01% (w/v) gelatin) and mixed on a rocking platform for 2 to 4 hours at 4° C. to elute the phage from the agar. The titer of the phage extract was determined, and the phage was replated at a sufficiently low density to allow for isolation of a single positive plaque. Plates with low plaque density were rescreened in a manner identical to the screening procedure outlined above (i.e., filter overlay, incubation with primary and secondary antibodies, and NBT-BCIP treatment). The filter was then aligned with plate, and a single plaque corresponding to the positive signal was removed and transferred to Phage Extraction Buffer. The titer of the extract was determined as before, and the phage was replated at a sufficiently high density to cause complete lysis of E. coli Y1090 lawn on a 50 mm plate. Two to three ml Phage Extraction Buffer was added to the plate and mixed on a rocking platform at 4° C. for 2 to 4 hours to extract phage from the agar. The phage extract was then centrifuged at 10,000 g to remove contaminating bacteria, and the supernatant was stored at 4° C. over a layer of CHCl$_3$.

B. Large Scale Preparation of Recombinant Phage and Extraction of DNA

Large scale phage lysates of each of the positive recombinant phages were prepared as follows: One hundred ml of NZCYM medium (Sambrook et al., Molecular Cloning: A Laboratory Manual, Cold Spring Harbor Laboratory Press, NY (1989)) was seeded with a single colony of E. coli Y1090 cells, and incubated at 37° C. with vigorous shaking, till the cell density reached $8 \times 10^8$ cells/ml (i.e., OD$_{600}$=1). An aliquot containing $10^{10}$ cells was centrifuged at 4000g for 10 minutes at room temperature, and resuspended in 3 ml SM (Sambrook et al., ibid.). The cells were then infected with $5 \times 10^7$ recombinant phage and incubated at 37° C. for 20 minutes, after which the infected cells were transferred to 500 ml of pre-warmed NZCYM. The culture was incubated at 37° C. with vigorous shaking till extensive lysis of the cells was evident (typically 2.5 hr for λ-gt11 recombinants in E. coli Y1090). Ten ml CHCl$_3$ was added and incubation was extended for an additional 30 minutes at 37° C. with vigorous agitation to ensure that the culture was completely lysed. DNAase and RNAase were added to a final concentration of 1 μg/ml and the culture was incubated at room temperature for 30 minutes. NaCl was dissolved in the lysed culture to give a final concentration of 1 M and the culture was left standing in an ice bath for 1 hour, following which, polyethylene glycol (PEG; MW=8000) was dissolved to give a final concentration of 10% (w/v). The culture was left in an ice bath for additional 1 hr to precipitate the recombinant phage. The precipitated phage was recovered by centrifugation at 11,000 g for 10 minutes at 4° C. and resuspended in 8 ml SM. The suspension was extracted with an equal volume of CHCl$_3$ to remove PEG, and the aqueous phase containing the recombinant phage was centrifuged at 85,000 g for 2 hours at 4° C. The phage pellet was resuspended in 2 ml SM and rocked overnight at 4° C. to ensure complete resuspension. To extract DNA from the recombinant phage, EDTA and proteinase K were added to the phage suspension to give final concentrations of 20 mM and 50 μg/ml, respectively. The mixture was incubated at 65° C. for 1 hour and extracted first with an equal volume of phenol:chloroform (1:1 mixture saturated with 10 mM Tris-HCl pH 8.0, 1 mM EDTA) and then with an equal volume of TE (10 M Tris-HCl pH 8.0, 1 mM EDTA) saturated CHCl$_3$. The aqueous phase was dialyzed exhaustively against TE. The phage DNA in the dialysate was precipitated with 2.5 volumes of ethanol in presence of 0.2 M NaCl and rinsed with 70% ethanol to remove excess salt. The DNA was resuspended in 500 μl TE.

The cDNA insert from the recombinant phage was amplified by polymerase chain reaction (PCR). The PCR was performed in a 50 μl reaction with 1 ng of the purified phage DNA using 50 pmol each of λ-gt11 forward sequencing primer, SEQ ID NO:1, (located 13 to 27 bp upstream of the EcoRI site of λ-gt11) and λ-gt11 reverse sequencing primer, SEQ ID NO:3, (located 8 to 22 bp downstream of the EcoRI site) as oligonucleotide primers, 10 mM Tris-HCl (pH 8.3), 50 mM KCl, 1.5 mM MgCl$_2$, 0.01% (w/v) gelatin, 200 μM each of dATP, dCTP, dGTP, and dTTP and 2.5 U Taq DNA polymerase. Only the larger (545 bp) of the two cDNA inserts was further processed for subcloning. After amplification of the cDNA insert by PCR, 2 U of Klenow fragment (large fragment of DNA polymerase I) (Promega Corp., Madison, Wis.) were added to the reaction. Then the reaction was incubated at room temperature for 15 minutes to fill in the staggered ends that persist after PCR owing to incomplete extension in the PCR reaction. The filled-in cDNA fragment from the PCR reaction was then electrophoresed in a 1% low-melting-point agarose gel, excised from the gel, and purified from the gel slice using glass slurry. The purified insert cDNA was dissolved in 10 to 20 μl sterile deionized water.

C. Subcloning of PCR Fragment into SmaI Site of pGEM7Zf(+)

The vector was prepared by digesting 1 μg pGEM7Zf(+) with 5 U of SmaI in a 10 μl reaction at 37° C. for 1 hour. The reaction was extracted with a mixture of phenol:chloroform. The DNA in the aqueous phase was precipitated with 2.5 volumes of ethanol in the presence of 0.3 M sodium acetate. The DNA precipitate was washed with 70% ethanol, dried, and dissolved in 50 μl sterile deionized water. Ligation of the cDNA insert to the vector was carried out in a 10 μl reaction containing 30 mM Tris-HCl (pH 7.8), 10 mM MgCl$_2$, 10 mM DTT, 1 mM ATP, 20 pmol vector [i.e., SmaI digested pGEM7Zf(+)], 40 pmol purified cDNA insert, and 2 U T4 DNA ligase. The reaction was incubated at room temperature for 12 to 16 hours. The ligation reaction was diluted five fold with TE and 2 μl were used to transform competent E. coli INIalphaF' cells (Invitrogen Corp., San Diego, Calif.) [endA1, recA1, hsdR17(rk ,mk+), supE44, thi1, gyrA, relA1, Φ80lacZΔM15, Δ(lacZYA-argF), F] using a BIO-RAD electroporator according to directions provided by the manufacturer. Several putative positive clones were analyzed by restriction analysis of plasmid DNA isolated from small-scale cultures of bacteria harboring the recombinant plasmid (Zhou et al., BioTechniques 8(2):

172–173 (19901). The authenticity of a recombinant plasmid was confirmed by sequence analysis.

The longer of the two cDNA clones (designated pG7kc7, FIG. 1) was sequenced in its entirety. The 545 bp cDNA insert was a partial clone, coding for 113 C-terminal amino acids of the mature protein, and the entire 3′-noncoding region.

D. Rescreening of the eDNA Library to Obtain Full-Length eDNA Clones

In order to obtain full-length cDNA clones of human κ-casein, the original cDNA library was rescreened with $^{32}P$-labeled RNA transcripts made from the partial clone as described by Yoshimura and Oka, Gene 78:267–275 (1989). $^{32}P$-labeled RNA was synthesized in a 20 μl reaction containing 20 mM Tris-HCl (pH 7.5), 3 mMMgCl$_2$ 1 mM spermidine, 5 mM NaCl, 10 mM DTT, 40 U RNASIN ribonuclease inhibitor (Promega Corp.), 0.1 mM each of ATP and CTP, 0.05 mM GTP, 1 m MP$^1$-5′-(7-Methyl)-guanosine-P$^3$-5′-guanosine triphosphate (m$^7$GpppG), 75 μM UTP, 50 μCi $^{32}P$-UTP (3000 Ci/mmol; NEN), 1 μg pG7kc7 (linearized with EcoRI), and 5 U SP6 RNA polymerase. The reaction was incubated at 30° C. for 2.5 hours and the specific activity of the probe was computed. The initial steps for rescreening the cDNA library were identical in all respects to the screening procedure with antibodies outlined above, except that nitrocellulose filters were not treated with IPTG. After removal of the filters from the plates the filters were air-dried and baked for 4 hours at 80° C. The baked filters were transferred to a hybridization pouch (KAPAC; VWR) containing 20 ml hybridization buffer (0.5M NaCl, 0.1 M Na$_2$HPO$_4$ (pH 7.0), 5 mM EDTA 1% sarcosyl, 100 μg/ml denatured herring sperm DNA; 4 ml per filter) and sealed. The filters were prehybridized for 20 min at 65° C., after which, 2×10$^7$ dpm $^{32}P$-labeled RNA probe was injected into the pouch. The filters were hybridized at 65° C. for 12 to 16 hours with gentle shaking. The filters were then washed three times for 15 minutes each, in 1 liter volumes of 1 mM Tris-HCl (pH 8.0), 1% sarcosyl at room temperature with vigorous agitation. The filters were air-dried, covered with SARAN WRAP and exposed overnight to KODAK film XAR-5 with a CRONEX LIGHTNING PLUS (DUPONT) intensifying screen.

Over 50 positive signals were obtained. Each of the positive phage plaque areas was identified by aligning the autoradiograms on the plates with the help of the orientation marks. The high density of the plaques on the plates precluded the isolation of a single plaque corresponding to the positive signal. The positive plaque areas (usually containing 15 to 20 plaques) were transferred to tubes containing 500 μl Phage Extraction Buffer. Then they were gently mixed on a rocking platform at 4° C. for 4 hours to elute the phage. The estimated size of the portion of human κ-casein cDNA not represented in pG7kc7 was approximately 350 bp, from interspecies comparisons of κ-casein cDNAs. In order to eliminate the need to purify each of the over 50 plaques to determine which of the recombinant phages were full-length, 5 μl aliquots from several of the phage eluates were subjected to PCR. PCR was performed under the same buffer conditions outlined above with 50 pmol forward sequencing primer or reverse sequencing primer and κ-casein cDNA primer AA75-80B, SEQ ID NO:5, as PCR primers. Two PCR reactions for each area had to be set up, one with the forward sequencing primer and AA75-80B and the other with reverse sequencing primer and AA75-80B since the orientation of the cDNA in the phage was unknown. Oligonucleotide AA75-80B is an antisense primer to the region of the κ-casein cDNA coding for amino acids 75 to 79 and the first two nucleotides coding for amino acid 80. The primer was designed from sequence information obtained from the original partial cDNA clone pG7kc7. The products of the PCR reactions were analyzed on a 1% agarose gel to identify reactions that yielded a fragment of approximately 400 bp (taking into account the extra nucleotides contributed by the PCR primers and the intervening λ-gt11 sequence). One such reaction in which positive plaque area 1.2(1) was used as PCR template yielded a fragment of about 400 bp. The PCR fragment was filled in with Klenow fragment, and subcloned into the SmaI site of pGEM7Zf(+), yielding a recombinant plasmid pG7kcl.2(1).

Figure 2:
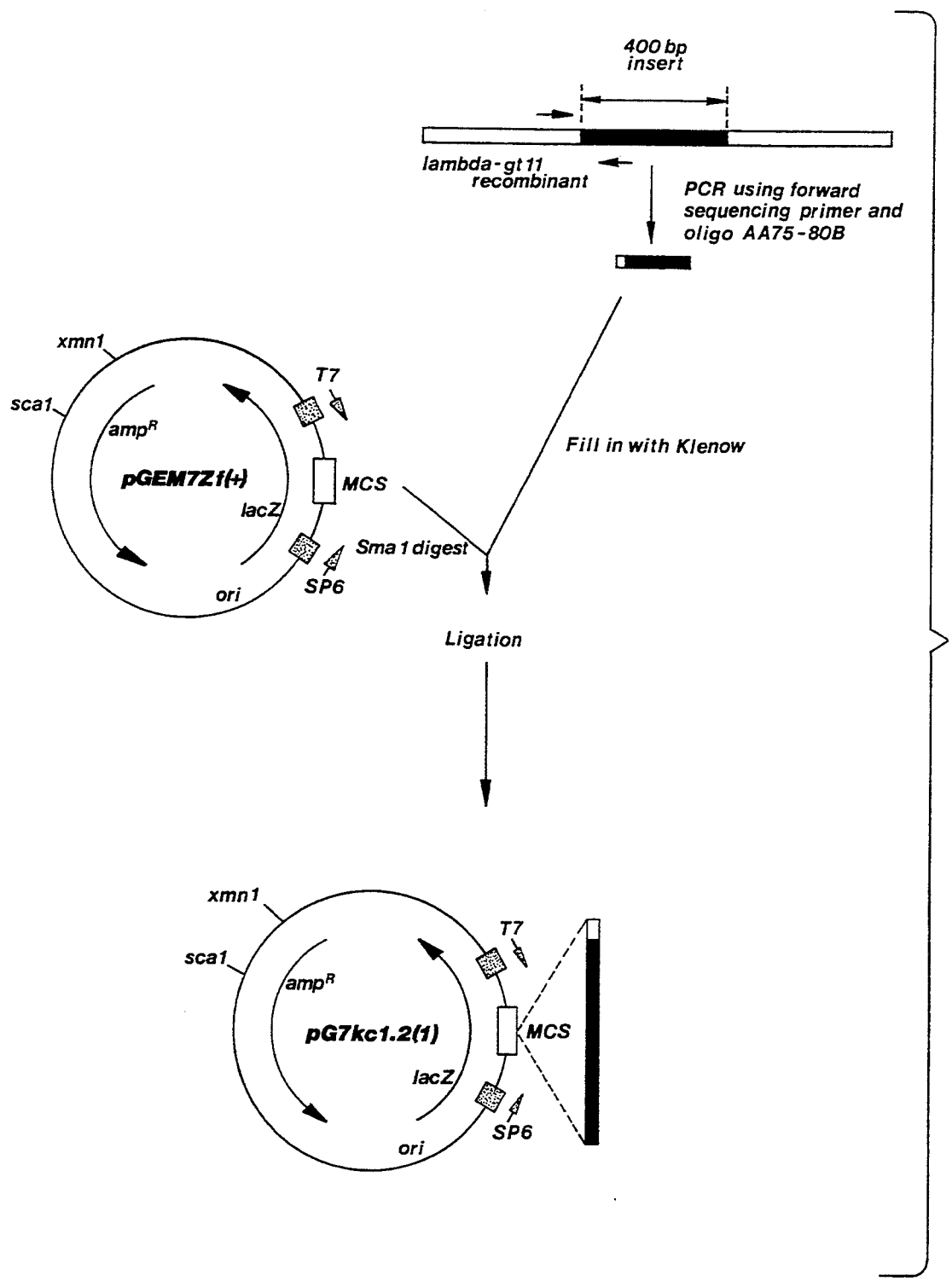
FIG. 2 shows the construction of a plasmid clone with a 400 bp cDNA insert extending from the first nucleotide of the 5'-noncoding region, to the first two nucleotides coding for amino acid 80 of the mature human κ-casein protein.
Figure 3:
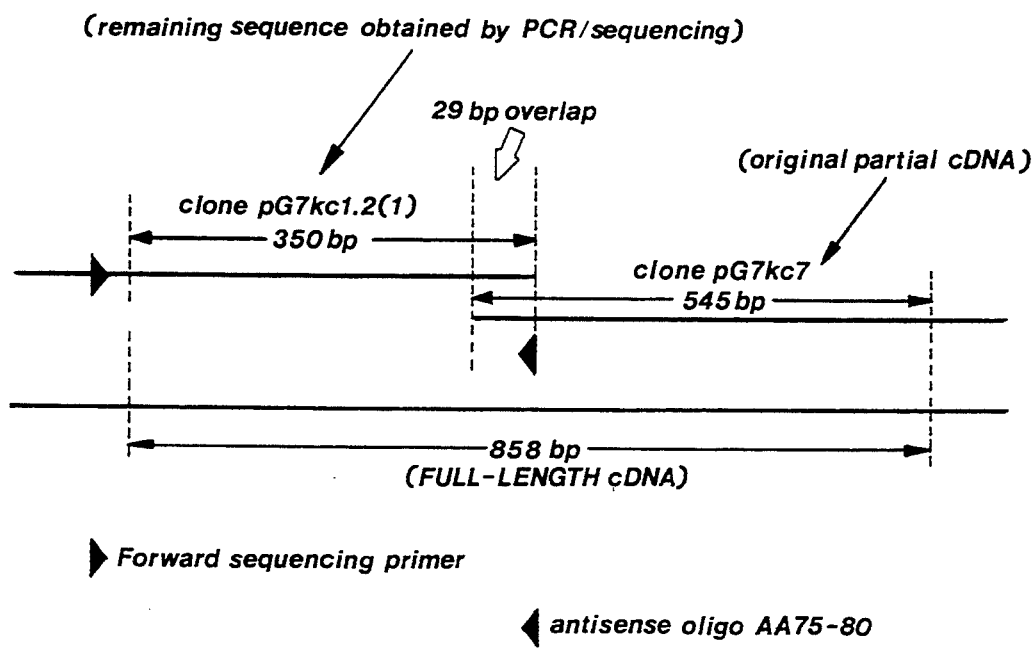
FIG. 3 is a schematic representation of the two cDNA clones in relation to the full-length cDNA sequence of the mature human κ-casein protein.

The 400 bp insert in the recombinant plasmid pG7kcl.2(1) contains the entire 5′noncoding region of human κ-casein. The insert extends through the first two nucleotides that code for amino acid 80 of the mature human κ-casein protein (FIG. 2). There is a 29 base pair overlap between the cDNA clones pG7kc7 and pG7kcl.2(1) (FIG. 3 ).

E. Sequence Analysis of Recombinant Plasmids

The recombinant plasmids were sequenced in both directions by a modified version of the Sanger dideoxy method provided in the SEQUENASE kit by the manufacturer (US Biochemical Corp., Cleveland, Ohio). The manufacturer's protocol recommends purification of the DNA template by cesium chloride centrifugation. The modified version eliminates the time-consuming purification step and outlines a rapid small-scale plasmid DNA preparation that routinely yields DNA of sufficient purity to give unambiguous sequence information. E. coli harboring the recombinant plasmid was grown overnight in 2 ml LB containing 100 μg/ml ampicillin. The overnight culture (1.5 ml) was spun down in a microcentrifuge and the medium was aspirated. The cells were resuspended in 100 μl ice cold buffer containing 50 M glucose, 10 mM EDTA, and 25 mM Tris-HCl (pH 8.0). After 5 min at room temperature, 200 μl of a freshly prepared solution of 0.2 M NaOH, 1% SDS was added. The viscous samples were mixed by inversion and incubated on ice for 5 minutes. One hundred and fifty μl of ice cold potassium acetate (pH 4.8) were added and the sample was vortexed briefly. The sample was centrifuged at 4° C. and the supernatant was transferred to a fresh microfuge tube. R3Aase A was added to a final concentration of 50 μg/ml. The sample was incubated at 37° C. for 30 minutes. The sample was then extracted with phenol:chloroform and the aqueous phase was precipitated with 2.5 volumes of chilled ethanol. The precipitated plasmid DNA was centrifuged and rinsed once with 70% ethanol. The DNA pellet was dried under vacuum and dissolved in 16.8 μl sterile deionized water. The plasmid DNA was reprecipitated by the addition of 3.2 μl of 5 M NaCl and 20 μl of 13% (w/v) PEG-8000. The sample was centrifuged to pellet the DNA and rinsed with 70% ethanol. The DNA pellet was dried under vacuum and dissolved in 20 μl sterile deionized water. The entire volume was used for DNA sequencing. Two μl of a freshly prepared solution of 2 M NaOH and 2 mM EDTA was added to the DNA solution. The tube was incubated for 5 min at room temperature to denature the double-stranded DNA. The solution was then neutralized with 8 μl of 1 M Tris-HCl (pH 4.5) and precipitated with 3 μl of 3 M sodium acetate and 75 μl chilled ethanol. The sample was incubated on dry ice for 20 minutes. The tube was then centrifuged at 4° C. for 5 minutes. The DNA pellets were rinsed with 70% ethanol. The pellets were dried under vacuum. The following components were added: 10 ng SP6 or T7 promotor primer (sequencing primer), 2 μl 5 × SEQUENASE Buffer, and 7 μl sterile deionized water. The sample was mixed and incubated at 37° C. for 30 minutes. While the annealing mix was incubating, 2.5 μl Termination mixes (ddATP, ddCTP, ddGTP, ddTTP) were aliquoted into tubes marked appropriately and incubated at 37° C. The following components were then added to the annealing mix: 1 μl 0.1 M DTT, 2 μl Labeling mix (diluted 1:15 with water), 0.5 μl (4 μCi) [$^{35}$S]dATP, and 2 μl of 1:8 dilution SEQUENASE). The labeling reaction was incubated at room temperature for 5 minutes. Three-and-a-half μl aliquots of the labeling reaction were transferred to each of the termination mix tubes and incubation was continued at 37° C. for 5 minutes. The sequencing reactions were terminated by the the addition of 4 μl Stop Solution. The sequencing reactions were heated at 70° C. and quick chilled prior to loading onto an 8% polyacrylamide-8M Urea gel. After the run, the gel was fixed in 10% acetic acid (v/v):12% methanol (v/v) in water, dried and exposed to HYPERFILM β-MAX film (Amersham Corp.) for 12 to 16 hours.

F. Construction of a Full-Length eDNA Clone for Human κ-Casein

Figure 4:
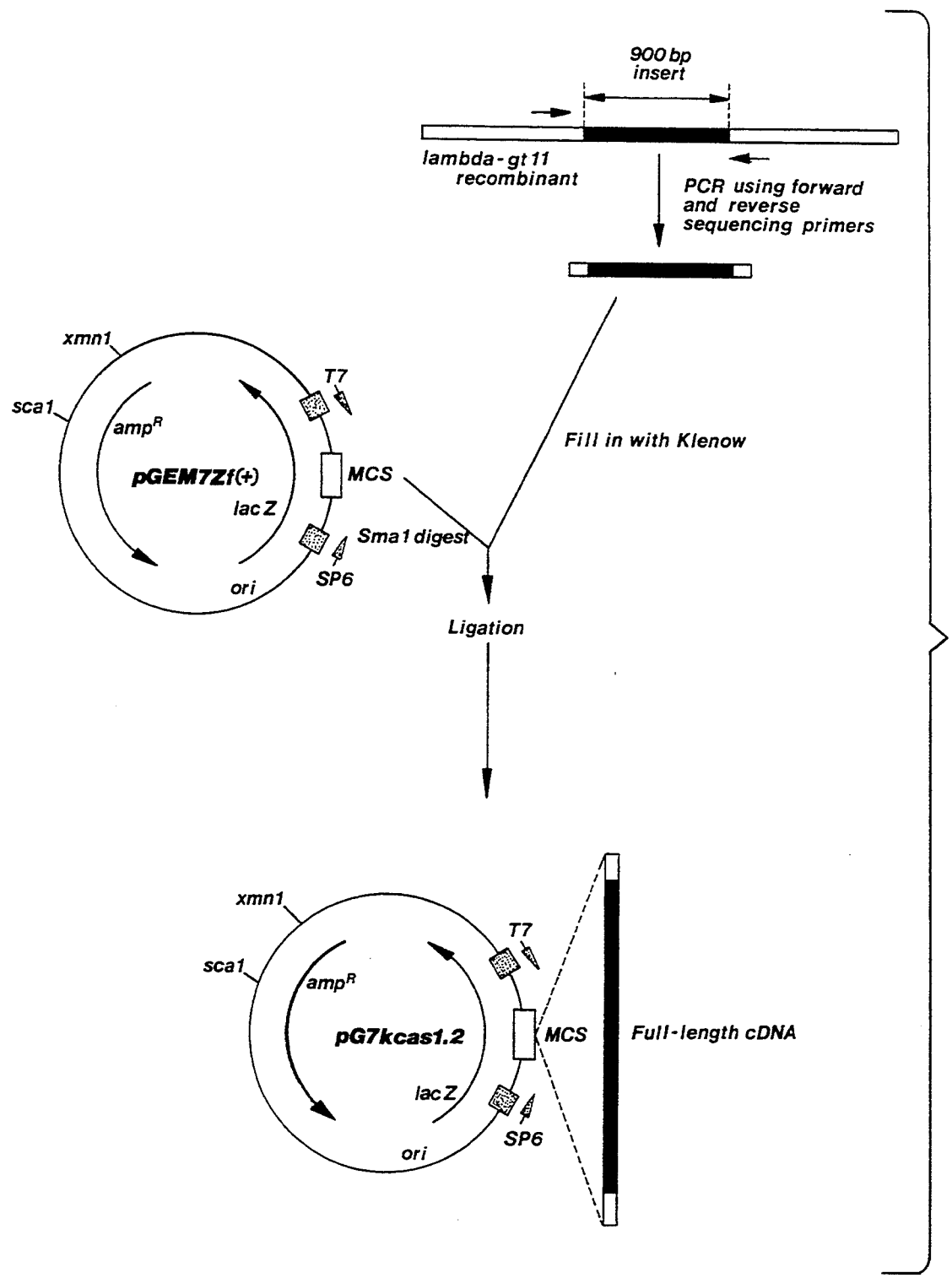
FIG. 4 shows the construction of a plasmid with a 900 bp cDNA insert coding for the mature human κ-casein protein and the flanking λ-gt11 sequence.

An aliquot (5 μl) of the phage eluate from plaque area 1.2(1) was used as template in a PCR reaction under buffer conditions identical to the previous PCR reactions described above with forward and reverse sequencing primers as PCR primers. PCR extended for 30 cycles, following which the product was analyzed on a 1% agarose gel. A product of approximately 900 bp was obtained, which is the expected size for a full-length cDNA clone for human κ-casein plus the flanking λ-gt11 sequence. The PCR fragment was filled in with Klenow fragment, gel purified, and subcloned into the SmaI site of pGEM7Zf(+) as described above (FIG. 4). The full-length cDNA clone, designated pG7kcasl.2, was sequenced in its entirety, as shown in SEQ ID NO:7 (FIG. 5), and showed no discrepancy with the complete nucleotide sequence reconstructed from the previous two clones; pG7kc7 and pG7kc1.2(1).

DEPOSIT OF STRAINS USEFUL IN PRACTICING THE INVENTION

A deposit of biologically pure cultures of the following strain was made with the American Type Culture Collection, 12301 Parklawn Drive, Rockville, Md., the accession number indicated was assigned after successful viability testing, and the requisite fees were paid. Access to said culture will be available during pendency of the patent application to one determined by the Commissioner to be entitled thereto under 37 C.F.R. Section 1.14 and 35 U.S.C. Section 122. All restriction on availability of said culture to the public will be irrevocably removed upon the granting of a patent based upon the application and said culture will remain permanently available for a term of at least five years after the most recent request for the furnishing of a sample and in any case for a period of at least 30 years after the date of the deposit. Should the culture become nonviable or be inadvertently destroyed, it will be replaced with a viable culture(s) of the same taxonomic description.

| Strain Plasmid | ATCC No. | Deposit Date |
| --- | --- | --- |
| full length cDNA for human k-casein E. coli INV1alphaF' | 69044 | August 5, 1992 |

The technology now exists to produce large quantities of human milk proteins in transgenic animals, such as cows, sheep, goats, and pigs. Kappa-casein is one of these proteins. The invention of the cDNA and its protein-coding sequence can be used in achieving that goal.

As will be apparent to those skilled in the art in which the invention is addressed, the present invention may be embodied in forms other than those specifically disclosed above without departing from the spirit or essential characteristics of the invention. The particular embodiments of the present invention described above, are, therefore, to be considered in all respects as illustrative and not restrictive. The scope of the present invention is as set forth in the appended claims rather than being limited to the examples contained in the foregoing description.

We claim:

1. A cDNA sequence encoding human κ-casein.
2. A DNA vector comprising a DNA sequence encoding human κ-casein.
3. The vector of claim 2, said vector being a plasmid.
4. A cDNA sequence according to claim 1 having the protein coding region set forth in Seq. ID No:7.

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 1..15

( x i ) SEQUENCE DESCRIPTION: SEQ ID NO:1:

GAC TCC TGG AGC CCG    15
Asp Ser Trp Ser Pro
1                5

( 2 ) INFORMATION FOR SEQ ID NO:2:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

Asp Ser Trp Ser Pro
1                5

( 2 ) INFORMATION FOR SEQ ID NO:3:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 1..15

( x i ) SEQUENCE DESCRIPTION: SEQ ID NO:3:

GGT AGC GAC CGG CGC    15
Gly Ser Asp Arg Arg
1                5

( 2 ) INFORMATION FOR SEQ ID NO:4:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

Gly Ser Asp Arg Arg
1                5

( 2 ) INFORMATION FOR SEQ ID NO:5:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 1..15

( x i ) SEQUENCE DESCRIPTION: SEQ ID NO:5:

GTG CGA GGC ACA TAT GG    17
Val Arg Gly Thr Tyr
1                5

( 2 ) INFORMATION FOR SEQ ID NO:6:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

| Val | Arg | Gly | Thr | Tyr |
|-----|-----|-----|-----|-----|
| 1   |     |     |     | 5   |

( 2 ) INFORMATION FOR SEQ ID NO:7:

( i ) SEQUENCE CHARACTERISTICS:
        ( A ) LENGTH: 858 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 107..656

( x i ) SEQUENCE DESCRIPTION: SEQ ID NO:7:

```
GCCTGGTGAT AGCTGGTTGT CCAAGATAGA ATCTTAGTTC AACTTTAAAT TTGCCAGCTC        60

AACCTACTGC CAACCAAGAC CTGACTGGCA CGAGGAAGGT GCAATA ATG AAG AGT         115
                                                   Met Lys Ser
                                                     1

TTT CTT CTA GTT GTC AAT GCC CTG GCA TTA ACC CTG CCT TTT TTG GCT         163
Phe Leu Leu Val Val Asn Ala Leu Ala Leu Thr Leu Pro Phe Leu Ala
      5                  10                  15

GTG GAG GTT CAA AAC CAG AAA CAA CCA GCA TGC CAT GAG AAT GAT GAA         211
Val Glu Val Gln Asn Gln Lys Gln Pro Ala Cys His Glu Asn Asp Glu
 20                  25                  30                  35

AGA CCA TTC TAT CAG AAA ACA GCT CCA TAT GTC CCA ATG TAT TAT GTG         259
Arg Pro Phe Tyr Gln Lys Thr Ala Pro Tyr Val Pro Met Tyr Tyr Val
                 40                  45                  50

CCA AAT AGC TAT CCT TAT TAT GGA ACC AAT TTG TAC CAA CGT AGA CCA         307
Pro Asn Ser Tyr Pro Tyr Tyr Gly Thr Asn Leu Tyr Gln Arg Arg Pro
             55                  60                  65

GCT ATA GCA ATT AAT AAT CCA TAT GTG CCT CGC ACA TAT TAT GCA AAC         355
Ala Ile Ala Ile Asn Asn Pro Tyr Val Pro Arg Thr Tyr Tyr Ala Asn
         70                  75                  80

CCA GCT GTA GTT AGG CCA CAT GCC CAA ATT CCT CAG CGG CAA TAC CTG         403
Pro Ala Val Val Arg Pro His Ala Gln Ile Pro Gln Arg Gln Tyr Leu
     85                  90                  95

CCA AAT AGC CAC CCA CCC ACT GTG GTA CGT CGC CCA AAC CTG CAT CCA         451
Pro Asn Ser His Pro Pro Thr Val Val Arg Arg Pro Asn Leu His Pro
100                 105                 110                 115

TCA TTT ATT GCC ATC CCC CCA AAG AAA ATT CAG GAT AAA ATA ATC ATC         499
Ser Phe Ile Ala Ile Pro Pro Lys Lys Ile Gln Asp Lys Ile Ile Ile
                120                 125                 130

CCT ACC ATC AAT ACC ATT GCT ACT GTT GAA CCT ACA CCA ACT CCT GCC         547
Pro Thr Ile Asn Thr Ile Ala Thr Val Glu Pro Thr Pro Thr Pro Ala
            135                 140                 145

ACT GAA CCA ACG GTG GAC AGT GTA GTC ACT CCA GAA GCT TTT TCA GAG         595
Thr Glu Pro Thr Val Asp Ser Val Val Thr Pro Glu Ala Phe Ser Glu
        150                 155                 160

TCC ATC ATC ACG AGC ACC CCT GAG ACA ACC ACA GTC GCA GTT ACT CCA         643
Ser Ile Ile Thr Ser Thr Pro Glu Thr Thr Thr Val Ala Val Thr Pro
165                 170                 175

CCT ACG GCA TAA A AACACCAAGG AAATATCAAA GAACACAACG CAGGACTTGC           696
Pro Thr Ala
180

TGAAACCAAA TTACTACTTC ACACTCTCCT GCAGCCATTG TCTGCCTTCA GTCAACAGAA       756

ATGTGATTTT CACAGATTCA GCTCTTCTCT CCTTACATTT TACATTCATG CCACATTCAA       816
```

TATTTTGATT CTTGCACAAT AAAGCCAACT GATTGCAACC TG                858

( 2 ) INFORMATION FOR SEQ ID NO:8:

( i ) SEQUENCE CHARACTERISTICS:
        ( A ) LENGTH: 182 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

```
Met Lys Ser Phe Leu Val Val Asn Ala Leu Ala Leu Thr Leu Pro
 1           5                  10                 15

Phe Leu Ala Val Glu Val Gln Asn Gln Lys Gln Pro Ala Cys His Glu
            20                  25                 30

Asn Asp Glu Arg Pro Phe Tyr Gln Lys Thr Ala Pro Tyr Val Pro Met
            35                  40                 45

Tyr Tyr Val Pro Asn Ser Tyr Pro Tyr Gly Thr Asn Leu Tyr Gln
    50                  55                  60

Arg Arg Pro Ala Ile Ala Ile Asn Asn Pro Tyr Val Pro Arg Thr Tyr
 65                  70                  75                 80

Tyr Ala Asn Pro Ala Val Val Arg Pro His Ala Gln Ile Pro Gln Arg
                85                  90                  95

Gln Tyr Leu Pro Asn Ser His Pro Pro Thr Val Val Arg Arg Pro Asn
            100                 105                 110

Leu His Pro Ser Phe Ile Ala Ile Pro Pro Lys Lys Ile Gln Asp Lys
        115                 120                 125

Ile Ile Ile Pro Thr Ile Asn Thr Ile Ala Thr Val Glu Pro Thr Pro
130                 135                 140

Thr Pro Ala Thr Glu Pro Thr Val Asp Ser Val Val Thr Pro Glu Ala
145                 150                 155                 160

Phe Ser Glu Ser Ile Ile Thr Ser Thr Pro Glu Thr Thr Thr Val Ala
                165                 170                 175

Val Thr Pro Pro Thr Ala
                180
```